United States Patent [19]
Wood et al.

[11] Patent Number: 6,005,093
[45] Date of Patent: Dec. 21, 1999

[54] NON-NUCLEOSIDIC COUMARIN DERIVATIVES AS POLYNUCLEOTIDE-CROSSLINKING AGENTS

[75] Inventors: Michael L. Wood, Palo Alto; Peter C. Cheng, San Jose; Douglas Y. Thien, Menlo Park; David Albagli, Palo Alto, all of Calif.

[73] Assignee: Naxcor, Menlo Park, Calif.

[21] Appl. No.: 08/401,630

[22] Filed: Mar. 9, 1995

Related U.S. Application Data

[63] Continuation-in-part of application No. 08/046,568, Apr. 13, 1993, abandoned.

[51] Int. Cl.[6] .................................................... C07H 21/04
[52] U.S. Cl. .................. 536/24.3; 536/24.5; 549/280; 549/289; 558/199
[58] Field of Search .................................. 536/24.3, 24.5; 549/280, 289; 558/199

[56] References Cited

U.S. PATENT DOCUMENTS

| | | | |
|---|---|---|---|
| 4,196,281 | 4/1980 | Hearst et al. | 536/24.5 |
| 4,378,458 | 3/1983 | Gohlke et al. | 536/24.3 |
| 4,599,303 | 7/1986 | Yabusaki et al. | 435/6 |
| 4,617,261 | 10/1986 | Sheldon, III et al. | 435/6 |
| 4,713,326 | 12/1987 | Dattagupta et al. | 435/6 |
| 4,737,454 | 4/1988 | Dattagupta et al. | 435/6 |
| 4,822,731 | 4/1989 | Watson et al. | 435/6 |
| 4,826,967 | 5/1989 | Glass | 536/28.5 |
| 5,026,840 | 6/1991 | Dattagupta et al. | 536/25.32 |
| 5,082,934 | 1/1992 | Saba et al. | 536/17.6 |
| 5,112,963 | 5/1992 | Pieles et al. | 526/24.3 |
| 5,124,246 | 6/1992 | Urdea et al. | 435/6 |

FOREIGN PATENT DOCUMENTS

| | | |
|---|---|---|
| 0 324 616 | 7/1989 | European Pat. Off. |
| 2642074 | 7/1990 | France |
| 4114482 | 11/1992 | Germany |
| 1254855 | 11/1986 | Japan |
| 9008156 | 7/1990 | WIPO |
| 9012020 | 11/1990 | WIPO |
| 9213629 | 8/1992 | WIPO |
| WO 94/24120 | 10/1994 | WIPO |

OTHER PUBLICATIONS

Clontech Catalog 94/95, pp. 709, 113–116.

Ou et al. (I), "Photobinding of 8–Metoxypsoralens and 5,7–Dimethoxycoumarin to DNA and Its Effect on Template Activity," *Biochemistry*, 17(6), 1047–1053 (1978).

Ou et al. (II), "Photobinding of 8–Methoxypsoralens to Transfer RNA and 5–Fluorouracil–Enriched Transfer RNA," *Biochemistry*, 17(6), 1054–1059 (1978).

Lown et al., "Photoreactions of Psoralen and Other Furocoumarins With Nucleic Acids," *Bioorg. Chem.*, 7(1), 85–95 (1978); *Chem. Abstr.*, 88, p. 259, Abstr. No. 184809s (1978); Only Abstract provided.

Seidel et al. (I), "Nucleic Acid Base Specific Quenching of a Coumarin–120–Derivative in Nucleotide–Conjugates–Photoinduced Electron Transfer?" *Proc. SPIE–Int. Soc. Opt. Eng., (Biomol. Spectrose. 2)*, 1991, 91–104.

Seidel et al. (II), "Characterization of Fluorescence–Labeled DNA by Time Resolved Fluorescence Spectoscopy," *Proc. SPIE–Int. Soc. Opt. Eng., (Biomol. Spectrosc. 2)*, 1991, 105–116.

Alves, "A Chemical Method of Labeling Oligodeoxyribonucleotides with Biotin: A Single Step Procedure Using a Solid Phase Methodology," *Tett. Lett.*, 30(23), 3089–3092 (1989).

Boiziau et al., "Mechanisms of the Inhibition of Reverse Transcriptase by Antisense Oligonucleotides," *Proc. Nat. Acad. Sci. USA*, 89, 768–772 (1992).

Cimino et al., "Psoralens as Photoactive Probes of Nucleic Acid Structure and Function: Organic Chemistry, Photochemistry, and Biochemistry," *Ann. Rev. Biochem.*, 54, 1151–1193 (1985).

Cocuzza, "A Phosphoramidite Reagent for Automated Solid Phase Synthesis of 5'–Biotinylated Oligonucletides," *Tett. Lett.*, 30(46), 6287–6290 (1989).

Gamper et al., "Solution Hybridization of Crosslinkable DNA Oligonucleotides to Bacteriophage M 13 DNA— Effect of Secondary Structure on Hybridization Kinetics and Equlibria," *J. Mol. Biol.*, 197, 349–362 (1987).

Goodchild, "Conjugates of Oligonucleotides and Modified Oligonucleotides: A Review of Their Synthesis and Properties," *Bioconjugate Chem.*, 1(3), 165–187 (1990).

Haralambidis et al., "The Preparation of Polyamide–Oligonucleotide Probes Containing Multiple Non–radioactive Labels," *Nucleic Acids Res.*, 18(3), 501–505 (1990).

Lee et al., "Interaction of Psoralen–Derivatized Oligodeoxyribonucleoside Methylphosphonates with Single–Stranded DNA," *Biochemistry*, 27, 3197–3203 (1988).

Misiura et al., "Biotinyl and Phosphotyrosinyl Phosphoramidite Derivatives Useful in the Incorporation of Multiple Reported Groups on Synthetic Oligonucleotides," *Nucleic Acids Res.*, 18(15), 4345–4354 (1990).

Nelson et al. (I), "A New and Versatile Reagent for Incorporating Multiple Primary Aliphatic Amines into Synthetic Oligonucleotides," *Nucleic Acids Res.*, 17(18), 7179–7186 (1989).

Nelson et al. (II), "Bifunctional Oligonucleotide Probes Synthesized Using a Novel CPG Support Are Able to Detect Single Base Pair Mutations," *Nucleic Acids Res.*, 17(18), 7187–7194 (1989).

(List continued on next page.)

*Primary Examiner*—John Kight
*Assistant Examiner*—L Eric Crane
*Attorney, Agent, or Firm*—Cooley Godward LLP

[57] ABSTRACT

Novel coumarin derivatives comprising a coumarin moiety linked to a non-nucleosidic backbone moiety are disclosed. The resulting molecules are typically used as photoactivate cross-linking groups when incorporated into polynucleotides as replacements for one or more of the complementary nucleoside bases present in probes used in procedures involving nucleic acid hybridization reactions.

41 Claims, No Drawings

OTHER PUBLICATIONS

Nelson et al. (III), "Oligonucleotide Labelling Methods. 3. Direct Labeling of Oligonucleotides Employing a Novel, Non–Nucleosidic, 2–Amino–1,3–propanediol Backbone," *Nuclkeic Acids Res.,* 20(23), 6253–6259 (1992).

Pieles et al. (I), "Psoralen Covalently Linked to Oligodeoxyribonucleotides: Synthesis, Sequence Specific Recognition of DNA and Photo–Cross–Linking to Pyrimidine Residues of DNA," *Nucleic Acids Res.,* 17(1), 285–299 (1989).

Pieles et al. (II), "Preparation of a Novel Psoralen Containing Deoxyadenosine Building Block for the Facile Solid Phase Synthesis of Psoralen–Modified Oligonucleotides for a Sequence–Specific Crosslink or a Given Target Sequence," *Nucleic Acids Res.,* 17(22), 8967–8978 (1989).

Takasugi et al., "Sequence–Specific Photo–Induced Cross–Linking of the Two Strands of Double–Helical DNA by a Psoralen Covalently Linked to a Triple Helix–Forming Oligonucleotide," *Proc. Nat. Acad. Sci. USA,* 88, 5602–5606 (1991).

Suortti et al., "Necatorin, A Highly Mutagenic Compound from *Lacarius Necator,*" *Phytochemistry,* 22(12), 2873–2874 (1983).

NON-NUCLEOSIDIC COUMARIN DERIVATIVES AS POLYNUCLEOTIDE-CROSSLINKING AGENTS

CROSS REFERENCE TO RELATED APPLICATIONS

This is a continuation-in-part of U.S. patent application Ser. No. 08/046,568 filed Apr. 13, 1993, now abandoned. U.S. application Ser. No. 08/046,568 is herein incorporated by reference.

TECHNICAL FIELD

This invention is related to photoactive nucleoside analogues that can be incorporated into synthetic oligonucleotides during automated DNA synthesis for use in crosslinking of complementary target nucleic acid sequences.

BACKGROUND

The use of crosslinkable probes in nucleic acid hybridization assays to crosslink to target sequences is demonstrated in U.S. Pat. No. 4,826,967 by K. Yabusaki et al.; compounds are based on furocoumarin (or psoralen) attached to existing polynucleotides (usually through adduct formation) and are satisfactory for many applications. However, the crosslinking group/nucleoside adduct is difficult to synthesize, particularly in large quantities. In U.S. Pat. No. 5,082,934, Saba et al. describe a photoactivatible nucleoside analogue comprising a coumarin moiety linked through its phenyl ring to the 1-position of a ribose or deoxyribose sugar moiety in the absence of an intervening base moiety. The resulting nucleoside analogue is used as a photo-crosslinking group when inserted into a polynucleotide as a replacement for one or more of the complementary nucleoside bases present in a probe used in hybridization assays.

Nevertheless, new types of compounds that offer additional advantages, such as stability throughout probe synthesis and use, and conformational flexibility, continue to remain desirable.

SUMMARY OF THE INVENTION

The current invention provides non-nucleosidic, stable, photoactive compounds that can be used as photo-crosslinking reagents in nucleic acid hybridization assays and therapeutic applications, as well as techniques and intermediates that can be used to prepare the final products.

The compounds comprise coumarinyl derivatives prepared by linking the phenyl ring of a coumarin molecule or derivative to a hydroxy or polyhydroxy hydrocarbon molecule, such as one of the terminal hydroxy groups of a glycerol molecule. The (poly)hydroxy hydrocarbon moiety of the resulting compound is equivalent to the sugar of a nucleoside, while the coumarin moiety occupies the position of a base. Accordingly, the compounds can be inserted into growing polynucleotide chains using automated (or manual) techniques of polynucleotide synthesis. The double bond between the 3 and 4 positions of the coumarin ring system is a photoactive group that covalently crosslinks to nucleosides in the complementary strand when an oligonucleotide containing this non-nucleoside analogue (the "probe") is used in a hybridization assay and/or therapeutic application.

For the most part, the photoactive compound has the formula

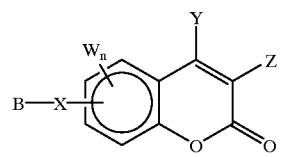

in which the substituents and linking groups are described below in more detail.

The (poly)hydroxy hydrocarbon backbones give maximum flexibility and stability to the oligosaccharide structure in which they are located as well as good solubility in aqueous and organic media.

DESCRIPTION OF SPECIFIC EMBODIMENTS

The present invention provides crosslinkable compounds that can be used as a photoactivatible non-nucleosidic crosslinker in oligonucleotide probes used in hybridization assays and/or therapeutic applications. In hybridization assays, the compounds of the inventions are typically used as part of synthetic DNA or RNA oligonucleotides to determine the presence or absence of a specific DNA and RNA base sequence in a sample. More specifically, this invention provides coumarin derivatives attached to a stable, flexible, (poly)hydroxy hydrocarbon backbone unit that act as photoactive crosslinking compounds in hybridization assays.

Compounds of the invention have the general formula:

Backbone moiety—Linking moiety—Crosslinking moiety

"Moiety" here and elsewhere in this specification indicates a part of a molecule that performs the indicated function. A given moiety is usually derived from another molecule by covalently linking together two or more molecules, with the identifiable remnants of the original molecules being referred to as "moieties." For example, if a psoralen molecule is attached to a glycerin molecule with a divalent linker, such as a methylene group, the resulting single molecule is referred to as being formed of glycerin, methylene, and psoralen moieties. It is not necessary, however, that the three moieties actually arose from three separate molecules, as discussed below. Thus "derived from" can refer to theoretical, as well as actual, precursors.

The crosslinking moiety will be derived from molecules having a fused benzopyrone structure, such as the following: (1) coumarin and its simple derivatives; (2) psoralen and its derivatives, such as 8-methoxypsoralen or 5-methoxypsoralen (at least 40 other naturally occurring psoralens have been described in the literature and are useful in practicing the present invention); (3) cis-benzodipyrone and its derivatives; (4) trans-benzodipyrone; and (5) compounds containing fused coumarin-cinnoline ring systems. All of these molecules contain the necessary crosslinking group (an activated double bond) located in the right orientation and at the right distance to crosslink with a nucleotide in the target strand. All of these molecules are coumarin derivatives, in that all contain the basic coumarin (benzopyrone) ring system on which the remainder of the molecule is based.

The linking moiety will normally be formed from a precursor that contains from 1 to 100, preferably 1 to 25, more preferably 1 to 10, atoms with functional groups at two locations for attaching the other moieties to each other. After reaction of the precursor to form the linking moiety, the total number of atoms in the shortest linking chain of atoms between the coumarin ring system and the backbone moiety (sugar substitute) is generally from 1 to 15, preferably 1 to 7, more preferably 1 to 3. Otherwise this part of the structure can vary widely, as this is essentially just a flexible linkage from the crosslinking moiety to the backbone moiety.

The linking moiety is most often a stable cyclic or acyclic moiety derived by reaction of a molecule bearing appropriate functional groups (usually at its termini) for linking the crosslinking molecule at one end and the backbone molecule at the other end. However, if sufficient functional groups are present in the backbone and crosslinking moieties, a precursor to the linking moiety need not be used (i.e., the backbone and crosslinking moieties can be connected by a covalent bond).

It should be recognized that description of a particular part of the final molecule as belonging to a particular moiety of those identified above is somewhat arbitrary and does not necessarily mean that there were three original molecules that reacted to form the final product. There are a number of coumarin derivatives, for example, that have a functionalized methyl or methoxy group attached to the coumarin ring that can react with a functional group on a backbone moiety precursor to form a product from only two starting materials. However, the resulting structure will generally appear to have three parts as indicated above: the backbone molecule that is incorporated into the sugar backbone of a polynucleotide, the crosslinking moiety that occupies the space occupied by a base in a normal nucleoside, and the atoms (i.e., the linking moiety) that join the two principal parts together. For the sake of convenience, the linking moiety is considered to consist of atoms between the ring atom of the crosslinking moiety at the point of attachment and the last carbon atom that clearly forms part of the backbone structure in the moiety that replaces the sugar molecule, which is usually the carbon atom bearing a hydroxyl group (or reaction product of a hydroxyl group) that is closest to the crosslinking moiety.

The backbone moiety, so called because it ultimately functions in place of the ribose or deoxyribose portion of the backbone of a polynucleotide, will generally have 1 to 3 (sometimes more) hydroxyl groups (or similar functional groups, as discussed below) attached to different $sp^3$-hybridized carbon atoms. The backbone moiety is generally uncharged so that it can function as a substitute for ribose or deoxyribose in the final modified nucleotide. Backbone moieties include but are not limited to the following: (1) linear hydrocarbon moieties such as a three-carbon propane unit or a longer hydrocarbon chain with appropriate functional groups, usually selected from the group consisting of —OH, —NH$_2$, —SH, —COOH, acid halides, and acid anhydrides, and (2) cyclic hydrocarbon moieties typically having a 5- to 7-membered carbon ring structure bearing one to three hydroxyl group or other functional groups as in (1) above. The functional groups are shown in the preceding sentence in unreacted form and will be present as derivatives of the indicated functional groups in many embodiments. The reactive functional groups mentioned above (other than —OH and —SH) are generally present only in intermediates; however, after reacting with other functional groups, they become stable groups or form covalent bonds to other parts of the molecule.

In addition to the basic structure described above, one or more coupling moieties can be attached to the backbone moiety to facilitate formation of bonds to existing or growing polynucleotide chains. The coupling moieties will typically comprise hydroxy coupling and/or protecting groups that are used in solution or solid-phase nucleic acid synthesis when the molecule in question is an intermediate being used in the preparation of a probe molecule. Typical coupling groups include phosphoramidite, phosphate, H-phosphonate, phosphorothioate, methyl phosphonate, trityl, dimethoxytrityl, monomethoxytrityl, and pixyl groups. Non-phosphorous coupling groups include carbamates, amides, and linear and cyclic hydrocarbon groups, typically connecting to the remainder to themolecule with heteroatom substituents, such as —COCH$_3$, —CH$_2$OH, —CF$_3$, —NHCH$_3$, and PO$_2$CH$_2$CH$_3$. For a review of such chemistry, see "Oligonucleotide Synthesis, A Practical Approach," M. J. Gait, ed., IRL Press Ltd., Oxford, Great Britain, 1984, which is herein incorporated by reference.

Preferred compounds of the invention have the formula:

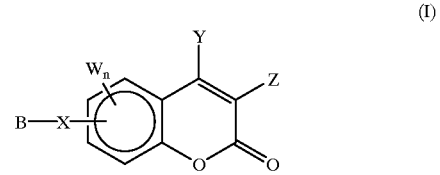

(I)

wherein
B represents (1) a linear, branched, or cyclic hydrocarbon group containing from 2 to 15, preferably 3 to 10, more preferably 3 to 6, carbon atoms and, if cyclic, containing a 5- or 6-membered ring or (2) a heterocyclic aromatic ring system comprising a 5- or 6-membered ring, both of B(1) and B(2) being substituted with 1, 2, or 3 groups of the formula OR$_1$;
X represents (1) a linear, branched, or cyclic hydrocarbon group containing 1 to 15, preferably 2 to 10, more preferably 3 to 6, carbon atoms or (2) such an X(1) group in which one to three (preferably one) carbon atom or atoms of the hydrocarbon group are replaced by an oxygen, sulfur, or nitrogen atom and in which the shortest linking chain of atoms in X between atoms in other parts of the formula attached to X is 1 to 10 atoms, wherein X is optionally substituted with 1–3 substituents selected from the group consisting of hydroxy, halogen, amino, amido, azido, carboxy, carbonyl, nitro, thio, perfluoromethyl, and cyano functional groups;
n is 0, 1, 2, or 3;
each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms, preferably 6 or fewer, more preferably 3 or fewer; or such a hydrocarbyl group substituted with 1–3 of the functional groups or in which one carbon atom is replaced by an oxygen, sulfur, or nitrogen atom;
with the provisos that (1) when X or W is a substituted hydrocarbon, the total number of substituents in X or W is less than the total number of carbon atoms in the X or W and no more than one substituent or heteroatom is attached to a given carbon, unless the substituents are halogen atoms on the given carbon; (2) the total carbon atoms in all W substituents is 15 or fewer, preferably 10 or fewer, more preferably 6 or fewer; and (3) two W's together can form a ring when taken together with the remainder of the atoms to which they are attached (e.g., as in a psoralen);
Y and Z independently represent H, F or lower alkyl (usually 5 of fewer carbons, preferably 3 or fewer); and each $R_1$ independently represent H, F or a hydroxy-protecting or hydroxy-coupling group capable of protecting or coupling a hydroxy group during synthesis of a polynucleotide or one or two (preferably two) $R_1$ represent a nucleotide or a polynucleotide connected to the compound.

The oxygen atom or other non-C atom (if present) of a functional group (such as an ether or carboxylate) that bridges the B-X linkage often arises from a hydroxyl group in the precursor of B, but is considered part of the X linker (for ease of defining the various groups) in this and the following formulas, unless the contrary is clear from the context of the discussion.

Within general formula I above, certain compounds are preferred. The most important part of the molecule (at least in view of the difference between these compounds and what was previously known) is the B or backbone moiety. Preferred B moieties belong to a group of a first sub-formula

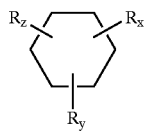

a group of a second sub-formula

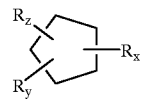

or a group of a third sub-formula

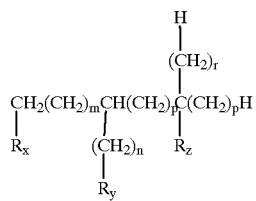

wherein s is 2 or 3;

$R_x$, $R_y$, and $R_z$ independently represent H or $OR_1$;

m, n, p, q, and r independently represent 0 or 1;

one hydrogen of the sub-formula is replaced by a covalent bond to the X group; and all other substituents and definitions of the formula of the compound are as previously defined for general formula I.

The hydrogen atom of the sub-formula that is replaced by a covalent bond to the X group is usually a hydrogen of a hydroxyl group (i.e, at least one $OR_1$ would represent a hydroxyl group in such a precursor molecule). However, this preference is for convenience of synthesis only, as the resulting B-X linkage can readily be prepared from (poly) hydroxy hydrocarbon precursors, many of which are commercially available. Other hydrogens can be replaced by the indicated covalent bond if desired. The actual molecules used in synthesis are often still derived from a (poly) hydroxy compound in which one of the hydroxyl groups has been replaced by the functional group, often through a series of reactions. For example, a hydroxyl group can be replaced by a halogen atom or other leaving group, and the leaving group can participate in bond formation with an electron donating group in the precursor of the X group.

Compounds in which B is formed from a saturated hydrocarbon are preferred, although unsaturated-compounds (including cyclic aromatics) are permitted. In unsaturated compounds (including aromatics), the $-OR_1$ substituent preferably is not attached directly to an $sp^2$-hybridized carbon, but is attached to an intervening $Sp^3$ carbon, as in $-CZ_2OR_1$ in which each Z represents H or an alkyl group.

Compound of formula I in which B has the third sub-formula are preferred among the three sub-formulas, especially those in which m+n+p+q+r=0, 1, or 2. Even more preferably, these compounds of the third sub-formula represent an acyclic, saturated, di- or tri-hydroxy hydrocarbon, especially glycerol and 1,2- or 1,3-dihydroxyalkanes of 3 to 5 carbons that are attached to the X group at their terminal position furthest from the indicated hydroxyl groups, such as 4,5-dihydroxypentyl, 3,5-dihydroxypentyl, 2,4-dihydroxy-2-methylbutyl, 3-hydroxy-2-(hydroxymethyl)propyl, and 2,3-dihydroxypropyl.

Although such compounds are not preferred, as already indicated, aromatic ring systems can be present in the B moiety. These include both hydrocarbon and hetererocyclic aromatic ring systems. Of these compounds in which B comprises a benzene or naphthalene ring system are preferred, especially 1,2-di(hydroxymethyl)-substituted aromatics. The same substituents are preferred when B comprises a heterocyclic ring system, such as a furan, pyran, pyrrole, pyrazole, imidazole, piperidine, pyridine, pyrazine, pyrimidine, pyrazidine, thiophene, acridine, indole, quinoline, isoquinoline, quinazoline, quinoxaline, xanthene or 1,2-benzopyran ring systems.

Also not preferred but within the scope of the invention are compounds in which B comprises a bridged hydrocarbon ring system, such as bicyclo [3.1.0] hexane or [2.2.1] heptane ring system. These molecules have configurations with reduced mobility so that various cis and trans substitution pattern can be easily prepared and maintained. See, for example, Ferguson, "Organic Molecular Structure," Willard Grant, Boston, 1975, chapters 17–19, for a review of this chemistry and synthetic techniques. In a like manner, compounds in which B comprises a spiro or dispiro hydrocarbon ring system are also within the scope of the invention.

As previously noted, the X linking group is not particularly restricted in structure, as it is not present in a part of the molecule that interacts either with the remainder of the backbone structure or with a complementary strand of a polynucleotide. However, there are preferred structures for this part of the molecule, such as the following, which can represent X, in either of the two possible orientations:

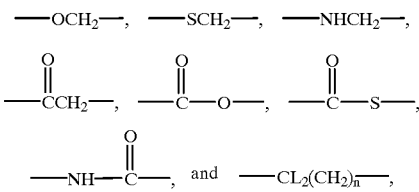

in which L represents H, F, Cl, I, or Br and n=0, 1, or 2.

Other (but lesser) preferred compounds are those in which X comprises a cyclic structure with a 5- or 6-membered carbon or heterocyclic ring (the latter containing one O, S, or N atom), such as cyclopentane, cyclohexene, dihydrofuran, pyrrole, or pyridine.

In the crosslinking moiety, Y and Z generally have 5 or fewer carbons, preferably 3 or fewer, and are most preferably methyl if they are alkyl groups. Compounds in which W, Y, and Z are all hydrogen are preferred, as are compounds in which W is a pyrone or furan ring fused to the phenyl ring of the formula. These later compounds are preferably compounds in which all of the formula to the right of X in formula I represents coumarin, psoralen, cis-benzodipyrone, or trans-benzodipyrone or a derivative thereof within the formula.

The compounds of formula I in which a nucleotide or polynucleotide is connected to the compound are usually (but not always) connected via a phosphorous-containing linking group. Preferred phosphorous-containing linking groups, as well as other linking groups, are discussed elsewhere. Such compounds are preferred compounds of the invention, as they can be used directly in the assays and crosslinking processes that are the principal end use of this invention. These compounds have the formula $(N_{m1}Q_{m4}N_{m2})_{m3}$ in which m1 and m2 are integers (usually less than 200, preferably less than 100; one of m1 and m2 is usually at least 14, preferably at least 17, most preferably at least 20); m3 is an integer from 1 to 10, preferably 1 to 5 (m3 is generally less than (m1+m2)/10); each N independently represents a nucleotide of a desired polynucleotide sequence; Q represents the nucleotide-replacing molecule of the invention incorporated into the normal polynucleotide sequence; and m4 is 1–5, preferably 1–3. It is also possible to have two or more Q moieties separated from each other by a few (usually one or two) normal bases in a polynucleotide sequence as long as there is an uninterrupted sequence of nucleotides to make the hybrid stable. Such sequences are considered to be equivalent to uninterrupted Q sequences. Preferred lengths of uninterrupted normal nucleotide sequences are as set out above for m1 and m2.

Q can be present either in the interior of the polynucleotide or at one of its terminal positions. In an interior position, at least two $R_1$ groups must be present in order to allow the Q molecule to connect to ends of two separate strands; if Q is inserted at a terminal position, only one $R_1$ is required, although others may be present in both cases.

In these formulas it should be recognized that each $N_{m1}Q_{m4}N_{m2}$ can differ from each other in a polynucleotide sequence in which m3 is greater than 1; i.e., multiple Q moieties can be present randomly along the length of a molecule, provided that the remaining parameters described above are complied with.

One group of preferred polynucleotides has a long sequence of uninterrupted normal bases with 1–5 Q moieties present at either or both ends of the molecule (preferably 1–3 Q moieties). As noted, the Q moieties can be either consecutive or can be interrupted with a few normal nucleotides. Plural Q moieties (either consecutive or not) in the middle of a probe also represents a preferred embodiment, with relatively long uninterrupted sequences to either side of the crosslinking Q units.

In all preferred embodiments, there is at least one uninterrupted sequence of nucleotides that is complementary to the corresponding target nucleotides. This uninterrupted sequence provides stability during the hybridization process so that proper recognition of the target will occur. The factors that lead to stability and selectivity are the same in the present process as in any other hybridization process. Uninterrupted sequences of complementary nucleotides followed by Q moieties are no different in this regard from uninterrupted sequences of target nucleotides followed by a non-complementary normal base. Thus, the stability of polynucleotides containing the crosslinking moiety of the invention can readily be predicted from standard considerations of nucleic acid hybridization.

Also preferred are compounds in which two R1 groups are present in the B moiety and both represent a different hydroxyl-coupling or hydroxyl-protecting group, as such compounds are ready for use in the synthesis of a crosslinkable polynucleotide. These protecting and activating groups are also discussed elsewhere in this specification.

Another particularly preferred group of compounds of the invention have the formula II below, many of which are within and a preferred embodiment of compounds of the scope of formula I:

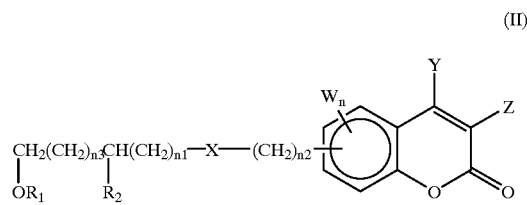

(II)

where $n_1$ is 0 to 10 (preferably 0 to 5, more preferably 1 to 3);

$n_2$ is 0 to 5 (preferably 0 to 2, more preferably 0 or 1);

$n_3$ is 0 to 5 (preferably 0 to 2, more preferably 0 or 1);

each W is independently a small stable substituent containing up to 15 atoms (especially a lower hydrocarbyl group; a halogen, nitro, thio, cyano, carbonyl, carboxy, hydroxy, amino, amido, or polyfluoroalkyl group; or a hydrocarbyl substituent containing one or more hetero atoms (i.e., an atom other than carbon or hydrogen that forms a stable covalent bond with carbon at 25° C. in water));

Y and Z independently represent H, F or a lower alkyl group;

X is an organic group containing (a) 1 to 10 carbon atoms and (b) 0 to 10, preferably 0 to 2, hetero atom selected from the group consisting of O, S and N, and wherein X comprises a shortest linking chain of 1 to 10 atoms between the other atoms of the formula to which it is attached;

$R_2$ is H or $OR_1$; and $R_1$ is H or a group capable of coupling with or protecting (the former preferably being located only on a terminal hydroxyl of the backbone moiety) a hydroxyl group during automated polynucleotide synthesis. Alternatively $R_1$ represents a nucleotide or polynucleotide linked to the compound by a phosphodiester linkage or other typical group used to couple sugars in polynucleotides. Preferred coupling groups include phosphorous containing groups such as phosphite, phospohramidite, phosphate, H-phosphonate, phosphorothioate, phosphorodithioate, and methyl phosphonate. Non-phosphorous coupling groups include carbamates and amides. Lower hydrocarbon groups include $C_1$–$C_6$ alkenyl and alkenyl group as well as $C_3$–$C_6$ cyclic groups, and preferably include $C_1$–$C_4$ alkyl and alkenyl groups, especially methyl, ethyl, propyl, isopropyl, butyl, iso-butyl, sec-butyl, and tert-butyl. Typical hydrocarbyl groups with hetero atom substituents include —$COCH_3$, —$CH_2OH$, —$CF_3$, —$NHCH_3$, —$CO_2CH_2CH_3$, and —$CON(CH_3)_2$.

Compounds of the invention are useful either as intermediates in the preparation of or as components of photoactivate polynucleotides used for example as probes in hybridization assays. Since the intention is that one or more of these molecules eventually form part of a polynucleotide, the backbone moiety that forms part of the molecules is derived either from glycerin or a different polyhydroxyl hydrocarbon molecule in most cases. The glyceryl or other polyhydroxyl hydrocarbon molecule is incorporated at any position into the backbone of a nucleic acid typically by phosphodiester type linkage with the 3' and/or 5' hydroxyl groups of the adjacent nucleotides in the molecule, with the crosslinking moiety normally being attached to the backbone moiety prior to such incorporation.

The crosslinking moiety portion of the compound of the invention can be derived from coumarin itself or any number of substituted coumarins. An organic functional group at the position in the crosslinking moiety precursor where glycerin or another backbone moiety will be attached is typically used to join the crosslinking moiety to the backbone moiety in the final product. Since final products can be often prepared by alternative synthetic routes, any given final product will likely have several possible precursors. The linking moiety can arise from a separate molecule or be formed by reaction portions of the crosslinking moiety precursor and the backbone moiety precursor.

At locations other than the linking position, the coumarin (or other) ring system can be either unsubstituted or substituted. Typical substitutents on the phenyl ring are small, stable substitutents normally found on aromatic rings in organic compounds. Substitutents can be selected as desired to change the excitation wavelength of the coumarin. Substitutents at the 3- and 4- positions are typically non-polar and are most often hydrocarbon substitutents, with methyl substitutents being most common. Although the location of coumarin substitutents can vary, substitutents are most often found at the 4-,5-,6–7, and 8-positions.

In certain preferred embodiment the coumarin moiety precursor, prior to reaction with the backbone moiety precursor, will have the formula:

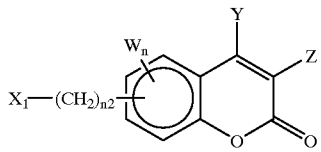

in which

Y, Z, $n_2$, M and W have the meanings previously defined; and $X_1$ is a precursor of all or part of the X linking moiety. $X_1$ will react with an organic function group on the precursor of the linker moiety to form a covalent bond. Typical reactive functional groups include hydroxy, amine, halogen, thio, carbonyl, carboxy ester, carboxy amide, silyl and vinyl groups. These precursors can be synthesized by standard methods of organic synthesis from coumarin itself or from the many commercially available coumarin derivatives.

In certain preferred embodiments the glycerol backbone moiety precursor has the formula:

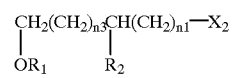

in which $R_1$, $R_2$, and $n_1$, and $n_3$ have the meaning previously defined and $X_2$ is a precursor of all or part of the X linking group.

$X_2$ will react with an organic functional group on the coumarin moiety to form a covalent bond in the final linking X moiety. $X_2$ typically will be selected from reactive functional groups and nucleophilic and electrophilic groups that are capable of undergoing nucleophilic or electrophilic substitution or addition. Examples of specific functional groups include hydroxy, amino, halogen, thio, carbonyl, carboxy ester, carboxy amide, vinyl, and silicon derivatives. This precursor can be synthesized by standard methods of organic synthesis from (poly)hydroxy hydrocarbons such as glycerin, commercial available 1,2- or 1,3-dihydroxy alkane derivatives, or such compounds with a protected hydroxyl group at the location of the indicated hydroxyl groups. See Misiura, K., Durrant, I., Evans, M. R., and Gait, M. J., Nucleic Acids Res. (1990) 18, 4345–4354, which is herein incorporated by reference, for a discussion of attaching moieties having structures similar to those of the present backbone moieties to bases used in polynucleotide synthesis.

Compounds of the invention can be prepared by standard techniques of synthetic organic chemistry, using the guidelines outlined in this specification. For example, a typical synthesis based on commercially available starting materials is set forth in the following reaction scheme.

REACTION SCHEME FOR TYPICAL SYNTHESIS

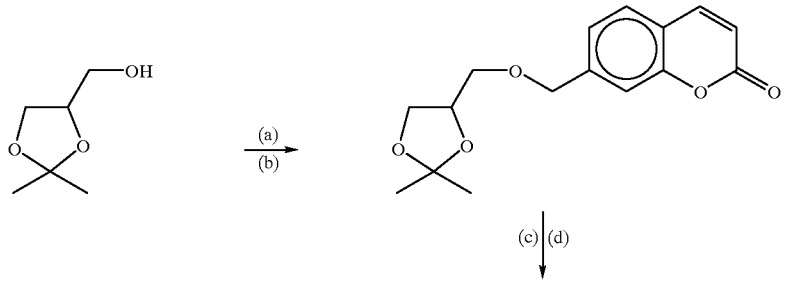

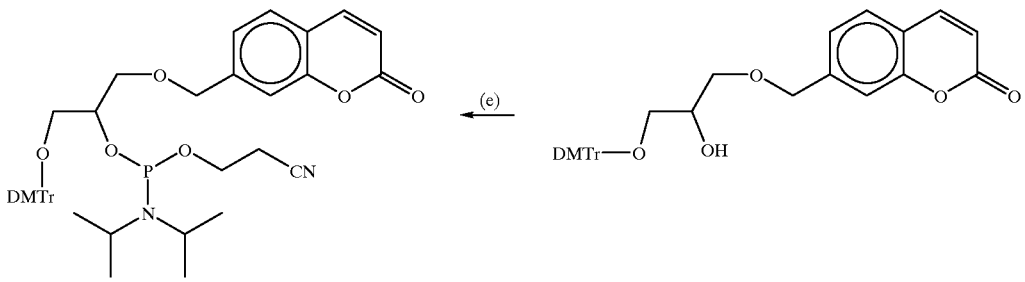

Reagents
(a) sodium hydride (NaH)/CH$_3$—O—CH$_2$CH$_2$—O—CH$_3$
(b) 7-bromomethyl coumarin
(c) HCl (aq.), THF (tetrahydrofuran)
(d) DMTrCl (4,4'-dimethoxytritylchloride), pyridine
(e) ClPN(ipr)$_2$OCH$_2$CH$_2$CN, CH$_3$CH$_2$N(ipr)$_2$, CH$_2$Cl$_2$

EXAMPLE 1

7-Coumarinyl methyl solketal

To 120 g ethylene glycol dimethyl ether was added solketal (2.64 g, 19.0 mmole) and sodium hydride (0.88 g, 22.0 mmole, 60% in mineral oil). To the resulting suspension was added 7-bromomethylcoumarin (4.8 g., 19.0 mmole) in small portions over a period of 7 minutes. After 10 min. 1.5 ml of glacial acetic acid was added to stop the reaction. The solid was then separated from the suspension solution by centrifugation. The solution was then concentrated to a solid. The solid was then purified by silica gel chromatography using chloroform/ethyl acetate 97:3 as the eluant. The fractions containing product were identified by TLC and were combined and concentrated to a white solid in vacuo. Yield was 630 mg; the melting point was 75–80° C. $R_f2$=0.55 in CHCl$_3$/ethylacetate 9:1.

EXAMPLE 2

1-O-(4,4'-dimethoxytrityl)-3-O-(7-coumarinyl methyl) glycerol

7-Coumarinyl methyl solketal (800 mg, 2.74 mmole) was dissolved in a solution of tetrahydrofuran (12 ml) and in hydrochloric acid (6 ml) for 20 minutes. The solution was then dried by co-evaporation with absolute ethanol (2×5 ml) to give an oil. The resulting solution was washed with 25 ml of saturated sodium carbonate solution and then extracted with 3×25 ml of diethyl ether. The solution was concentrated to an oil in vacuo. The oil was dried by co-evaporation with pyridine (2×5 ml) to give a dry product. To the liquid was added pyridine (30 ml), 4-dimethylaminopyridine (25 mg) and triethylamine (200 μl). To the resulting solution was added 4,4'-dimethoxy trityl chloride (905 mg, 2.95 mmole). The reaction mixture was stirred for two hours. 37.5 ml of water was added to stop the reaction, and the resulting solution was extracted with 2×180 ml of diethyl ether. The combined ether extracts were concentrated in vacuo, dissolved in 15 ml methylene chloride, and purified by silica gel chromatography using acetone/hexane 4:6 as the elution solvent. Fractions with $R_f$=0.5 were collected and evaporated to dryness to yield the product (770 mg, 55% yield).

EXAMPLE 3

1-O-(4,4'-Dimethoxytrityl)-3-O-(7-coumarinylmethyl)-2-O-[(N,N-diisopropyl)(2-cyanoethyl) phosphoramidite)]-glycerol 1-O-(4,4'-Dimethoxytrityl)-3-O-(7-coumarinylmethyl) glycerol (1.20 g, 2.18 mmole) was co-evaporated with 2×6.5 ml mixed solution (5 ml pyridine and 1.5 methylene chloride) two times. To the dry reactant was added methylene chloride (4.6 ml) and diisopropylethylamine (1.87 ml, 8.59 mmole). The suspension was stirred until it became a clear solution. Then, 2-cyanoethyl N,N-diisopropyl chlorophosphoramidite (0.62 ml, 3.24 mmole) was added to the solution. The resulting solution was stirred for 65 min. The reaction mixture was then diluted with 45 ml of ethyl acetate and 2.2 ml triethylamine, extracted with 10% aqueous sodium carbonate (2×30 ml), and with saturated sodium carbonate (2×30 ml), and with saturated sodium chloride (2×30 ml). The organic phase was concentrated in vacuo. The resulting product was purified by silica gel chromatography with a solvent system (methylene chloride/diethyl ether/triethylamine 90:7.5:1). Fractions with $R_f$=0.73 were collected. The yield was concentrated in vacuo to a solid. Yield was 1.06 g (1.41 mmole, 64%).

EXAMPLE 4

Preparation of Oligodeoxynucleotides Containing a Non-Nucleosidic Coumarin Functionality Using the reagent prepared in Example 3, above, an oligonucleotide was prepared via the β-cyanoethylphosphoramidite method of DNA synthesis that was identical to a segment of human papilloma virus type 16, comprising nucleotides 397 to 417 of the E6 gene in which the 20th base (adenine) was replaced by 3-(7-coumarinylmethyl)glycerol.

After assembly, the oligonucleotides were cleaved from the solid support with 3 ml 30% NH$_4$OH for 1.5 h at room temperature. The ammonia solution was then heated at 55° C. for 1.5 h. After cooling, the NH$_4$OH was removed in vacuo. The crude oligonucleotide was purified to homogeneity by reversed phase high performance liquid chromatography.

The oligonucleotide was hybridized in 0.75 M NaCl buffer (20 μL) with a complementary 5'-$^{32}$P-labeled target oligonucleotide (molar ratio of probe/target=10:1) for 1 hour at 40° C. At this time the solution was irradiated with 302 nm wavelength light for 10 minutes. Denaturing polyacrylamide gel electrophoresis analysis of the irradiated mixture indicated that the level of photochemical crosslinking achieved with respect to the radiolabeled target was 80%. Control experiments with analogous oligonucleotides containing one of the nucleosidic coumarin derivative described in Saba et al., U.S. Pat. No. 5,082,934, were carried out in parallel. The optimal crosslinking efficiencies obtained with these reagents were 60%. Accordingly, the compound of the invention underwent photochemical crosslinking with 20% more efficiency (⅓ greater relative efficiency).

EXAMPLE 5

By following a similar reaction shown in the previous examples 1, 2, and 3, a product with the following structure could be synthesized as well.

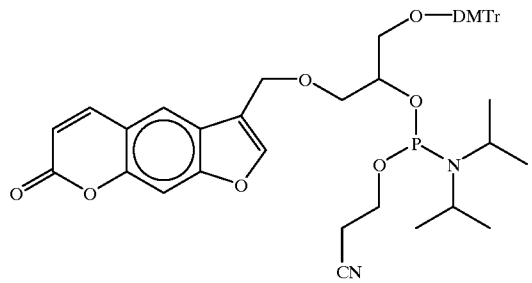

This compound would be also useful for the preparation of oligodeoxynucleotides containing non-nucleotide psoralen derivatives.

EXAMPLE 6

Using the reagent prepared in Example 3, oligonucleotides were prepared via the β-cyanoethylphosphoramidite method of DNA synthesis that were identical to segments of the genome of human papilloma virus type 16. The oligonucleotides were complementary to nucleotides 89-108 and 283-302 of the E6 gene, respectively (the sequence of which is herein incorporated by reference). In each molecule, the 5' terminal nucleotide of the natural sequence (adenosine) was replaced by 3-(7-coumarinylmethyl) glycerol. The 3' end terminated with a biotin moiety.

In parallel, two additional DNA molecules were synthesized. These oligonucleotides had complementary sequences to either nucleotides 89-108 or 283-302 of the E6 gene; however, in these modified oligonucleotides 3-(7-coumarinylmethyl) glycol was replaced by the nucleosidic coumarin derivative described in Saba et al., U.S. Pat. No. 5,082,934, by using the 3'-O-(N,N-diisopropyl phosphoramidite) 5'-O-(4,4'-dimethoxytrityl) derivative at the 5' position of the 2'-deoxyribonucleotide, herein referred to as the "Saba compound."

After assembly, the four oligonucleotides were cleaved from the solid support with 1 ml 30% NH$_4$OH for 1.5 hours at room temperature. The ammonia solution was then heated at 55° C. for a further 1.5 hours. After cooling, the NH$_4$OH was removed in vacuo. The crude oligonucleotides were purified to homogeneity by high performance liquid chromatography.

The oligonucleotides were hybridized in 0.75 M NaCl buffer (20 μl) with complementary 5'-$^{32}$P-labeled oligonucleotides (molar ratio of unlabelled:labelled oligonucletides=100:1) for 1 hour at 40° C. At this time the solutions were irradiated with UV-B wavelength light (XL 1500 UV cross-linker, Spectronics, Inc.) for 15 minutes. The extent of crosslinking (with respect to the radiolabeled targets) was determined by denaturing polyacrylamide gel electrophoresis followed by scintillation counting of the excised bands. The results are set forth in the following table:

| E6 Gene Sequence Position | Crosslinker Used in Oligonucleotide | Crosslinking Reaction Site 5'→3' | Crosslinking Efficiency 5 |
|---|---|---|---|
| 89–108 | 3-(7-Coumarinylmethyl) glycerol | TTT | 64% |
| 89–108 | Saba compound | TTT | 54% |
| 283–302 | 3-(7-Coumarinylmethyl) glycerol | TTT | 76% |
| 283–302 | Saba compound | TTT | 68% |

The results indicate that the compounds of the current invention undergo photochemical crosslinking more efficiently than the compound of U.S. Pat. No. 5,082,934 (>10% greater relative efficiency).

EXAMPLE 7

1-O-(4,4'-Dimethoxytrityl)-3-O-(7-coumarinyl)-2-O-(2-cyanoethyl-N,N-diisopropyl phosphoramidite) glycerol Another embodiment of the invention was synthesized using 7-hydroxycoumarin instead of 7-bromomethylcoumarin as in Example 1. The reaction scheme for the synthesis of 1-O-(4,4'-dimethoxytrityl)-3-O-(7-coumarinyl)-2-O-(2-cyanoethyl-N,N-diisopropyl phosphoramidite) glycerol is as follows:

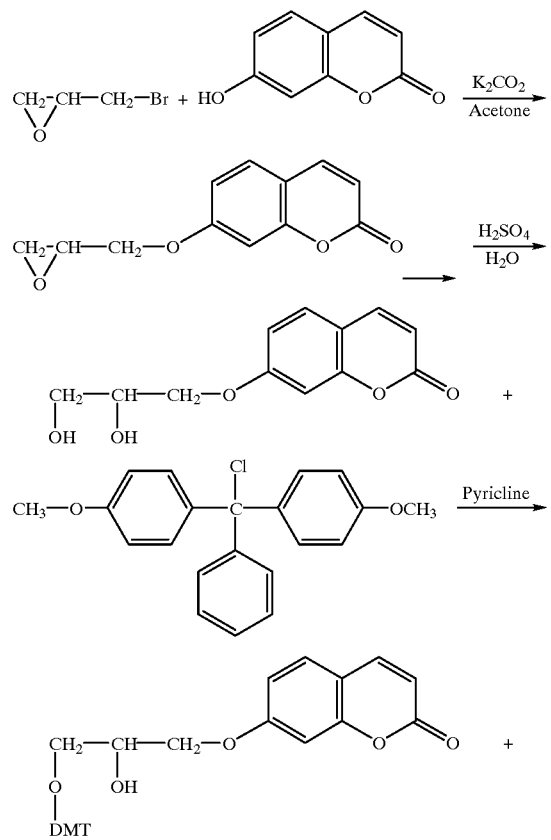

-continued

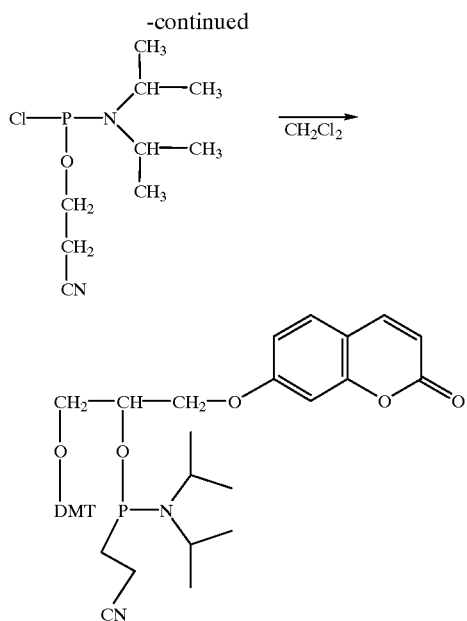

This synthetic route requires less time to complete than the reaction sequence using 7-bromomethylcoumarin and provides a cost savings of about 50 percent compared to the 7-bromomethylcoumarin synthetic sequence. The 7-hydroxycoumarin derivatives can be introduced into oligonucleotides and are more stable during deprotection of the oligonucleotides (exposure to concentrated $NH_3$ at room temperature) than compounds of U.S. Pat. No. 5,082,934. The 7-hydroxycoumarin derivatives exhibit a different absorption spectrum ($\lambda$ maximum of 325 nm) compared to the 7-bromomethylcoumarin derivatives ($\lambda$ maximum of 310 nm). The 7-hydroxycoumarin derivatives are red shifted relative to the 7-bromomethylcoumarin derivatives, which reduces the effect of quenchers, such as nucleic acids. The spectral shift also allows for more selective excitation of the 7-hydroxycoumarin derivatives.

Synthesis of 7-Glycidyl Coumarin

The intermediate 7-glycidyl coumarin was prepared in a reaction flask equipped with a reflux condenser containing 16.2 g of 7-hydroxycoumarin, 15.8 g of epibromohydrin, 13.8 g of potassium carbonate and 270 ml of acetone ("reaction solution"). The reaction solution was boiled and refluxed overnight, cooled, treated with 100 ml of 5% NaOH aqueous solution, and extracted three times with 80 ml of methylene chloride. After evaporating the solvent a crude yellow solid was obtained. The crude solid (1.5 g) was dissolved in a solution of 30 ml hexane and 20 ml acetone at 50° C. The hexane/acetone solution was then cooled at 0° C. for 2 to 3 hours. White crystals formed and were collected by filtering and dried to a white powder. 290 mg of white powder was obtained. The melting point of this new compound (7-glycidyl coumarin) was 110–112° C. Thin layer chromatography (TLC) was done in 8% (v/v) ethyl acetate/$CHCl_3$; the $R_f$ value of the 7-glycidyl coumarin was 0.6.

Hydrolysis of Glycidyl Coumarin

7-Glycidyl coumarin (2.0 g) was dissolved in a solution of 80 ml acetone and 50 ml of 1.8 M aqueous $H_2SO_4$. The acetone/acid solution was heated to a boil for 20 minutes. The solution was cooled and neutralized with a 1.6 M $NH_4OH$ aqueous solution until a pH 7–8 was reached. The neutralized solution was extracted with 50 ml ethyl acetate three times. After evaporating the solvent, the product, 7-(1-O-glyceryloxy)coumarin, was obtained with a melting point of 118–120° C.

Synthesis of 1-O-(4,4'-Dimethoxytrityl)-3-O-(7-coumarinyl) glycerol

Coumarinyl glycerol (1.37 g) was coevaporated with 11 ml of purified pyridine by rotary evaporation three times. The coevaporated coumarinyl glycerol was added to 44 mg 4-dimethylaminopyridine, 330 μl triethylamine, 45 ml pyridine and 1.78 g of dimethoxytrityl chloride. The solution was stirred at room temperature for 3 hours. The reaction was stopped by adding 66 ml of deionized water. The reaction solution was then extracted three times with 35 ml of methylene chloride. The organic phase was dried over sodium sulfate. The crude product obtained by evaporating the solvent was purified by chromatography using a silica gel column and eluting with a solution of 70% hexane, 28% acetone and 2% triethylamine. 2.6 g of purified product (1-O-(4,4' dimethoxytrityl)-3-O-(7-coumarinyl)glycerol) gave a single TLC spot with an $R_f$ of 0.43 using the same solvent system.

Synthesis of 1-O-(4,4'-dimethoxytrityl)-3-O-(7-coumarinyl)-2-O-(2-cyanoethyl-N,N-diisopropyl phosphoramidite) glycerol 1-O-4,4'-Dimethoxytrityl-3-O-(7-coumarinyl)glycerol (2.5 g) was coevaporated with 12 ml of 75% pyridine and 25% methylene chloride two times. A solution of 5 ml methylene chloride and 5 ml pyridine was added to the dry viscous liquid (methylene chloride/coumarin solution). The methylene chloride/coumarin solution was added under argon to a 50 ml flask containing a solution of 3 ml of diisopropylethylamine, 10 ml of methylene chloride and 1.8 g of 2-cyanoethyl N,N-diisopropyl chlorophosphoramidite. The solution was stirred for 90 minutes. The reaction mixture was diluted with a solution of 60 ml ethyl acetate and 3 ml triethylamine. The reaction mixture was extracted two times with 50 ml of saturated sodium chloride aqueous solution. The organic phase was then dried over sodium sulfate. The crude product was purified by a silica gel chromatography column. 2.6 g of purified product gave a single spot by TLC with an $R_f$ of 0.2 using 80% hexane and 20% acetone eluant.

EXAMPLE 8

Using the reagent prepared in Example 7, oligonucleotides were prepared via the β-cyanoethylphosphoramidite method of DNA synthesis that were identical to segments of the cryptic plasmid of *Chlamydia trachomatis*. The oligonucleotides were complementary to nucleotides 876-900, 6857-6878, 7118-7140, and 6725-6752 of the cryptic plasmid (the sequence of which is herein incorporated by reference), the first two oligonucleotides containing one crosslinking compound per oligonucleotide and the latter two oligonucleotides containing two crosslinking compounds per oligonucleotide.

After automated synthesis, the oligonucleotides were cleaved from the solid support and deprotected with 3 ml 30% $NH_4OH$ for 2 h at room temperature. The $NH_4OH$ was removed in vacuo, and the crude oligonucleotide was purified to homogeneity by denaturing polyacrylamide gel electrophoresis.

The oligonucleotides were hybridized in 0.75 M NaCl buffer (195 μl) with complementary 5'-$^{32}$P-labeled oligonucleotides (molar ratio of unlabeled:labeled oligonucleotides=100:1) for 20 minutes at 40° C., at which time the solutions were irradiated with UV-A wavelength light (8 W lamp) for 20 minutes. The extent of crosslinking (with respect to the radiolabeled oligonucleotide) was determined by denaturing polyacrylamide gel electrophoresis followed by scintillation counting of the exicsed bands. The results are set forth in the following table:

| Cryptic Plasmid of Chlamydia trachomatis | Number of Cross-linkers in Oligonucleotide | Crosslinking Reaction Site 5'→3' | Crosslinking Efficiency, % |
|---|---|---|---|
| 876–900 | 1 | TAA | 88 |
| 6857–6878 | 1 | TTT | 86 |
| 7118–7140 | 2 | TTT, TAT | 99 |
| 6725–6752 | 2 | TAC, TTT | 98 |

The results indicate that the compounds of the current invention undergo photochemical crosslinking more efficiently than the compound of U.S. Pat. No. 5,082,934.

EXAMPLE 9

Coumarin derivatives can be synthesized containing various side chains, including, (1) short side chains, such as glycerol, (2) long side chains, such as poly(ethylene glycols), (3) aromatic rings, and (4) aliphatic cyclic rings, such as ethylene-dioxy rings. Such coumarin derivatives can be synthesized from the approiate coumarin starting materials, such as, 7-methyl coumarin, 7-hydroxy coumarin, esculetin (6,7-dihydroxycoumarin) or 7-glycidyl coumarin. Attached to each coumarin starting material is the desired side chain containing active functional groups.

REACTION SCHEME FOR COUMARIN CONTAINING AN ALIPHATIC HETEROCYCLIC RING DERIVATIVE

1-O-[2-cyanoethyl-N,N-diispropyl phosphoramidite]-2,3-O-(6,7-coumarinyl)-glycerol This compound is not itself a compound within the general formulas described above, but is an intermediate that can be used to prepare such compounds via reaction of X and/or B unit precursors with the hydroxyl group that is activated by formation of a phosphoramidite in the last step of the reaction shown.

Reagent
(a) potassium carbonate/acetone
(b) potassium hydroxide
(c) 2-cyanoethyl N,N-diisopropyl chlorophosphoramidite/ diisopropylethylamine/pyridine
*mixture of Reaction at step (a) with 2,3-dibromo-1,4-dihydroxybutane instead of epibromohydrin gives the similar compound 2,3-O-(6,7-coumarinyl)-1,2,3,4-tetrahydroxybutane; which then can be converted to 1-O-O-(4,4'-dimethoxytrityl)-4-O-(β-cyanoethyl-N,N-diisopropyl phosphoramidite)-2,3-O,O-(6,7-coumarinyl)-1,2,3,4-tetrahydroxybutane as shown below.

Preparation Of 6,7-(Hydroxymethylethylenedioxy) coumarin (Steps AI & AII)

Esculetin (0.90 g) was stirred with a solution of potassium carbonate (1.40 g) and 200 ml of anhydrous acetone for 1 hour at room temperature. Epibromohydrin (1.05 g) was added to the solution. The yellow suspension solution was then refluxed overnight. Potassium hydroxide (0.70 g) was then added and refluxed for one hour. The solution was then separated from the solids by centrifugation. The solution was then evaporated by a water aspirator. The resulting product was then dissolved in 50 ml of water. The aqueous solution was then extracted three times with 35 ml of methylene chloride. The organic solution was extracted twice with 50 ml of 2M sodium hydroxide. The resulting organic phase was dried over sodium sulfate. After evaporating the solvent, 200 mg of white solid was obtained. TLC in 50% acetone/hexane shows $R_f$ 0.42. The yield was 26% by weight.

Preparation of Aliphatic Heterocyclic Ring Derivative (Step AIII)

6,7-(Hydroxymethylethylenedioxy)coumarin (200 mg) was coevaporated with 1 ml of dry pyridine, twice. To the dry reactant, 0.9 ml of dichloromethane and 0.9 ml of pyridine was added. 2-Cyanoethyl-N,N-diisopropyl chlorophosphoramidite (280 mg), was dissolved in a solution of 0.2 ml of diisopropylethylamine and 0.9 ml of dichloromethane. The phosphoramidite solution was added to the coumarin solution. The resulting solution was stirred at room temperature for 2 hours. The reaction mixture was then diluted with a solution of 10 ml of ethyl acetate and 0.5 ml of triethylamine. The solution was extracted three times with 6 ml of saturated sodium chloride solution. After evaporation of the solvent, the resulting product was purified by a silica gel column with the following eluant: acetone/hexane/triethylamine=36/60/4. The purified product (100 mg) was obtained with an $R_f$=0.57 (in TLC using the same eluant).

REACTION SCHEME FOR COUMARIN CONNECTED TO AN AROMATIC SIDE CHAIN

3-O-(7-Coumarinylmethoxy)-1-O-[2-cyanoethyl-N,N-diisoprophyl phosphoramidite]-1,3-dihydroxybenzene

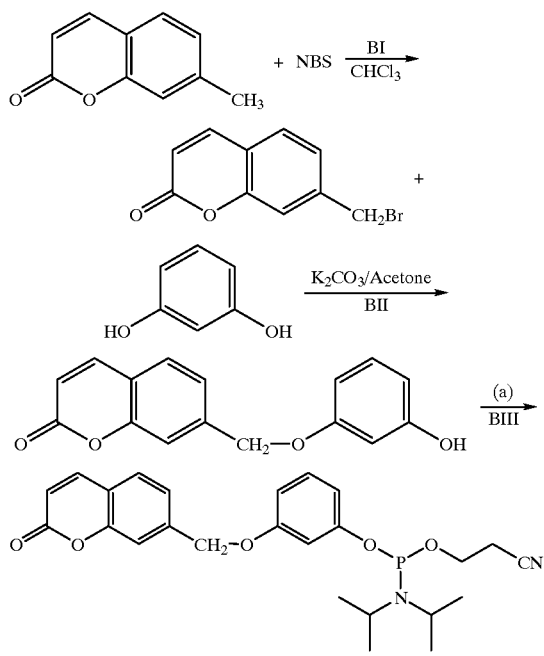

Reagents (a) 2-cyanoethyl-N,N-diisopropyl chlorophosphoramidite, diisopropylethylamine/pyridine/dichloromethane.

Preparation of 7-Bromomethyl Coumarin (Step BI)

7-Methylcoumarin (28 g), 70% benzoylperoxide (1.68 g), and N-bromosuccinimde (30.8 g) was added to 140 ml of chloroform in a one liter flask and the suspension was refluxed overnight. The solution was diluted with 100 ml of chloroform. The resulting crude product was recrystallized from 750 ml of acetone. A white solid (21 g) was obtained with a melting point of 172–176° C. was obtained.

Preparation of 3-O-(7-Coumarinylmethyl)-1,3-dihydroxybenzene (Step BII)

7-Bromomethylcoumarin (0.70 g) was added to a suspension of resorcinol (2.25 g), potassium carbonate (1.75 g) and acetone (200 ml). The solution was heated and stirred for 4 hours. The solution was then separated from the solid. After evaporating the solvent, the crude product was dissolved in 40 ml of dichloromethane. The organic solution was then extracted three times with 40 ml of water. TLC using 20% (v/v) ethyl acetate/chloroform gave $R_f$=0.32. After evaporating the solvent, the product was recrystallized from $CH_2Cl_2$/ethyl acetate solution; 300 mg of purified product was obtained.

Preparation Of 3-O-(7-Coumarinylmethoxy)-1-O-[2-cyanoethyl-N,N-diisopropyl phosphoramidite]-1,3-dihydroxybenzene (Step BIII)

2-cyanoethyl N,N-diisopropyl chlorophosphoramidite was reacted with the product of Step BII in a fashion similar to that of Step AIII.

REACTION SCHEME FOR COUMARIN CONTAINING A LONG SIDE CHAIN

3-O-(7-Coumarinyl)-2-O-(2-cyanoethyl-N,N-diisoprophyl phosphoramidite)-1-O-(2-[2-(4,4'-dimethoxytrityloxy)ethoxy]ethyl)glycerol

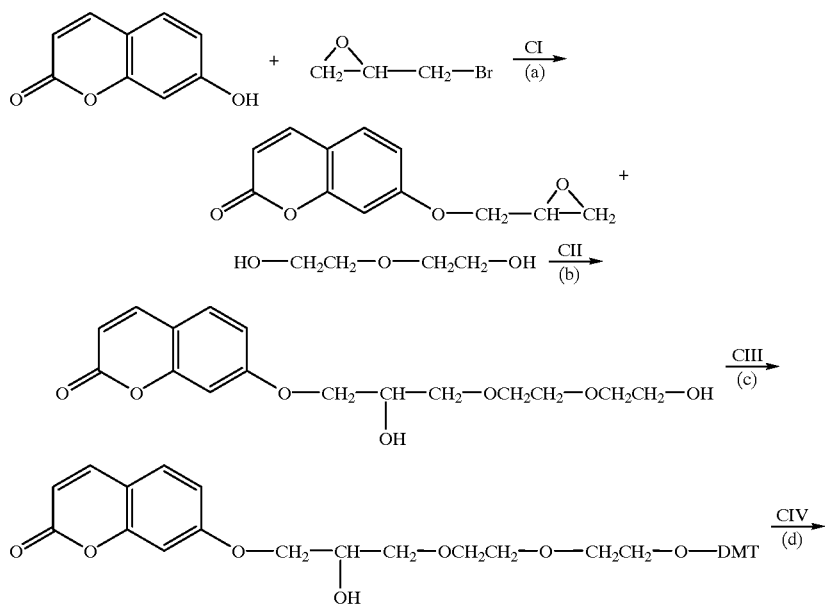

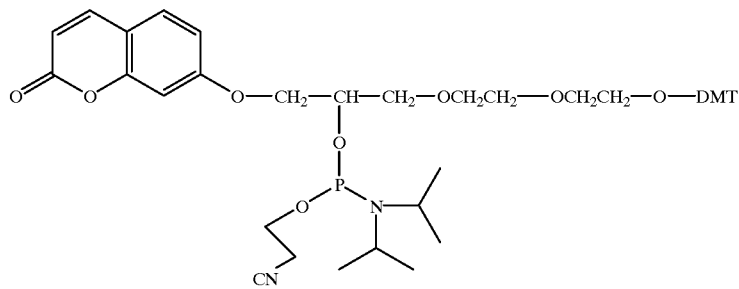

Reagents
(a) potassium carbonate/acetone
(b) sodium hydroxide/ethylene glycol dimethyl ether
(c) 4, 4'-dimethoxytritylchloride/pyridine
(d) 2-cyanoethyl N,N-diisopropyl chlorophosphoramidite, diisopropyl ethylamine/dichloromethane Preparation Of 7-Glycidyl Coumarin (Step CI)

This compound was prepared as described in Example 6.

Preparation Of 3-O-(7-Coumarinyl)-1-O-(2-[2-hydroxyethoxy]ethyl)glycerol(Step CII)

7-Glycidylcoumarin (1 g) was dissolved in a solution of 10 mg of sodium hydroxide, 2.65 g of diethylene glycol and 5 ml of ethylene glycol dimethyl ether. The solution was heated to reflux for 6 hours. The reaction mixture was diluted with 10 ml of de-ionized water and was extracted three times with 10 ml of dichloromethane. The organic phase was then dried over sodium sulfate. After evaporating the solvent, the crude product was then purified by a silica gel column with 50% (v/v) acetone/hexane. A major product with $R_f$ 0.09 (260 mg) and a minor product with $R_f$ 0.34 (50 mg) (TLC solvent 50% (v/v) hexane/acetone) were obtained.

Preparation Of 3-O-(7-Coumarinyl)-1-O-(2-[2-(4,4'-dimethoxytrityloxy)ethoxy]ethyl)glycerol (Step CIII)

The dihydroxy coumarin derivative (230 mg) obtained as the product of Step CII was coevaporated with dry pyridine. Dimethoxytritylchloride (320 mg), 60 ml of triethylamine and 10 mg of 4-dimethylaminopyridine were added to the coumarin derivative. The solution was stirred at room temperature for 16 hours. The solution was diluted with water and extracted with dichloromethane, then dried with sodium sulfate. After evaporating the solvent, the crude product was purified by a silica gel column with 40% (v/v) acetone/hexane as eluant.

Preparation Of 3-O-(7-Coumarinyl)-2-O-(2-cyanoethyl-N,N-diisopropyl phosphoramidite)-1-O-(2-[2-(4,4-dimethoxytrityloxy)ethoxy]ethyl)-glycerol (Step CIV)

2-Cyanoethyl-N,N-diisopropyl chlorophosphoramidite is reacted with the product of Step CIII as described in Step AIII.

Preparation Of Phosphoramidite Used In Steps AIII, BIII AND CIV

The general procedure for preparing the phosphoramidite is as follows. Under an inert atmosphere 1.2 eq of 2-cyanoethyl-N,N-diisopropyl chlorophosphoramidite and 2.4 eq of N,N-diisopropylethylamine are dissolved in 0.9 ml of dichloromethane in a glass container capped with a septum. The coumarin precursor (1.0 eq) (such as the product of steps AII, BII or CIII) was dissolved 9.9 ml of pyridine and 0.9 ml of dichloromethane. While the chlorophosphoramidite solution is stirred, the coumarin solution is added. Stirring is continued for 2 hours. Ethylacetate is added, and the organic solution is washed with NaCl (aqueous) three times and dried with $Na_2SO_4$. After removing the solvent, the crude product is purified by column chromatography using acetone/hexane/triethylamine (36:60:4). Appropriate fractions are collected and concentrated under vacuum.

The invention now being fully described, it will be apparent to one of ordinary skill in the art that many changes and modifications can be made thereto without departing from the spirit or scope of the appended claims.

All publications and patent applications mentioned in this specification are herein incorporated by reference to the same extent as if each individual publication or patent application was specifically and individually indicated to be incorporated by reference.

What is claimed is:

1. A compound having the formula:

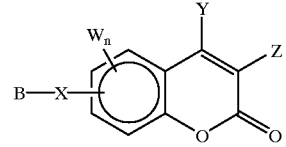

wherein

B represents (1) a linear, branched, or cyclic hydrocarbon group containing from 2 to 10 carbon atoms and, if cyclic, containing a 5- or 6-membered ring or (2) a heterocyclic aromatic ring system containing a 5- or 6-membered ring, said B(1) or B(2) being substituted with 2 or 3 groups of the formula $OR_1$, wherein $R_1$ independently represent H or a hydroxy-protecting or hydroxy-coupling group capable of protecting or coupling a hydroxy group during synthesis of a polynucleotide, or two $OR_1$ represent a nucleotide or a polynucleotide connected to said formula, and wherein one to three carbon atoms of the hydrocarbon group can be replaced by a nitrogen, or sulfur atom;

X represents (1) a bond, (2) a linear, branched, or cyclic hydrocarbon group containing 1 to 10 carbon atoms or (3) the X(2) group in which one to three carbon atoms of the hydrocarbon group are replaced by an oxygen, sulfur, or nitrogen atom and wherein the shortest linking chain of atoms in X between atoms in other parts of said formula attached to X is 1 to 10 atoms, wherein X is optionally substituted with 2–3 substituents selected from the group consisting of hydroxy, halogen, amino, amido, azido, carboxy, oxo, perfluoromethyl, and cyano functional groups; and wherein X is attached to the benzo ring of said formula directly or through W;

n is 0, 1, 2, or 3;

each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms; or said hydrocarbyl group substituted with 2–3 of said functional groups or in which one carbon atoms replaced by an oxygen, sulfur, or nitrogen atom and wherein two Ws together can represent a ring fused to the benzo ring of said formula;

with the provisos that (1) when X or W is a substituted hydrocarbon, the total number of substituents in X or W is less than the total number of carbon atoms in said X or W and no more than one substituent or heteroatom is attached to a given carbon, unless said substituents are halogen atoms on said given carbon, and (2) the total carbon atoms in all W substituents is 15 or fewer; and Y and Z independently represent H or lower alkyl or F;

wherein said formula contains one photoactive bond and said bond is located between the carbons to which Y and Z are attached in said formula.

2. The compound of claim 1, wherein X, in either orientation, is

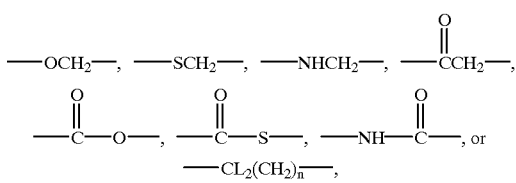

in which L=H, F, Cl, I, or Br and n=0, 1, or 2.

3. The compound of claim 1, wherein X is a cyclic structure with a 5- or 6- membered ring or a 5- or 6-membered heteroring containing one O, S, or N atom.

4. The compound of claim 1, wherein all of said formula to the right of X represents coumarin.

5. The compound of claim 1, wherein X is covalently connected to the 7 position of a coumarin moiety.

6. The compound of claim 1, wherein B represents:

a group of a first sub-formula

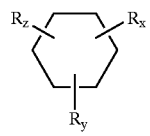

a group of a second sub-formula

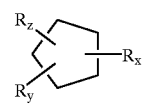

or a group of a third sub-formula

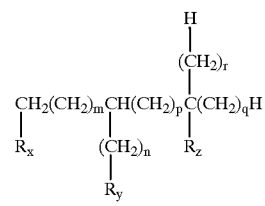

wherein $R_x$, $R_y$, and $R_z$ independently represent H or $OR_1$;

m, n, p, q, and r independently represent 0 or 1;

one hydrogen of said sub-formula is replaced by a covalent bond to said X group; and all other substituents and definitions of said formula of said compound are otherwise as previously defined.

7. The compound of claim 1, wherein B is saturated.

8. The compound of claim 6, wherein B has said third sub-formula.

9. The compound of claim 6, wherein m+n+p+q+r=0, 1, or 2.

10. The compound of claim 6, wherein said third sub-formula represents an acyclic, saturated, di- or tri-hydroxyhydrocarbon.

11. The compound of claim 6, wherein said third sub-formula represents tri-O-substituted glycerin.

12. The compound of claim 1, wherein said nucleotide or polynucleotide is connected to said compound via a phosphorous-containing linking group.

13. The compound of claim 12, wherein said phosphorous-containing group is a phosphate group.

14. The compound of claim 1, wherein B contains a benzene or naphthalene ring.

15. The compound of claim 1, wherein B contains a bridged hydrocarbon ring.

16. The compound of claim 1, wherein B contains a bicyclo [3.1.0] hexane or [2.2.1] heptane ring.

17. The compound of claim 1, wherein B contains a spiro or dispiro hydrocarbon ring.

18. The compound of claim 1, wherein at least one $R_1$ represents a trityl, pixyl, dimethoxytrityl, monomethoxytrityl, phosphite, phosphoramidite, phosphate, H-phosphonate, phosphorothioate, methylphosphonate, phosphodithioate or phosphotriester group.

19. The compound of claim 1, wherein B contains a heterocyclic ring selected from the group consisting of pyrrole, pyrazole, imidazole, piperidine, pyridine, pyrazine, pyrimidine, pyridazine, thiophene, acridine, indole, quinoline, isoquinoline and quinazoline.

20. A compound of claim 1, wherein said compound is a polynucleotide of the formula $(N_{m1}Q_{m4}N_{m2})_{m3}$ in which each N represents a nucleotide of a desired polynucleotide sequence, Q represents the nucleotide-replacing molecule in the formula of claim 1, and m1 and m2 are integers, wherein at least one of m1 and m2 is at least 14, m3 is from 1 to 10, and m4 is from 1 to 5.

21. A compound of claim 20 wherein m1 and m2 are less than 100.

22. A compound of claim 21 wherein at least one Q is at a terminal position and at least one Q is at an interior position of said polynucleotide sequence.

23. A compound of claim 21 wherein at least one Q is at a interior position of said polynucleotide sequence.

24. A compound of claim 21 wherein Q is at a terminal position of said polynucleotide sequence.

25. A compound having the formula:

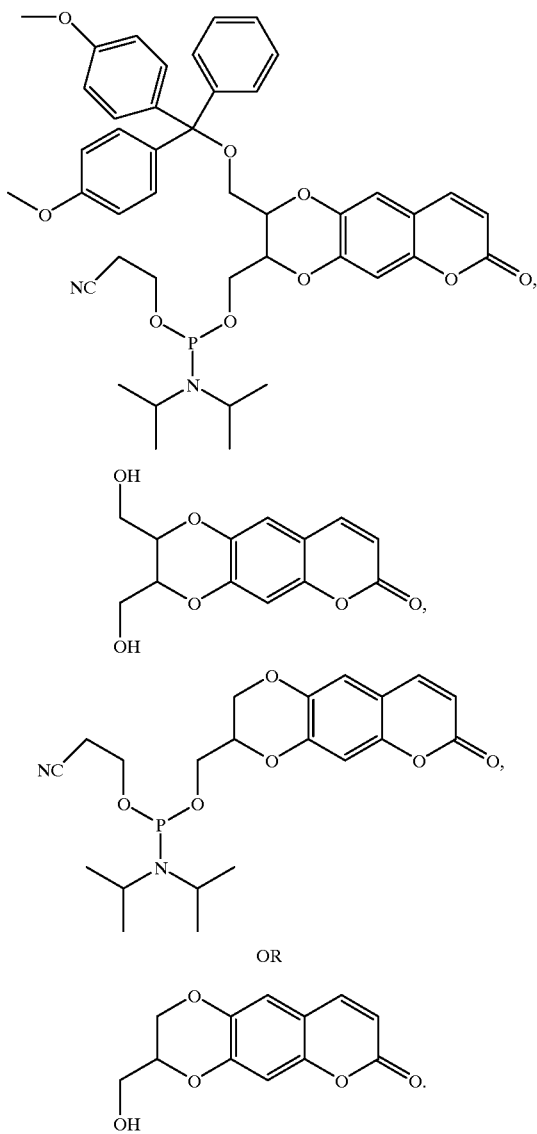

26. A compound of claim 1 wherein X is —CH$_2$—O— and B is

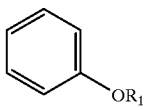

27. A compound having the formula:

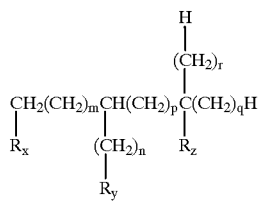

wherein
B represents (1) a branched or cyclic hydrocarbon group containing from 3 to 10 carbon atoms and, if cyclic, containing a 5- or 6-membered ring or (2) a heterocyclic aromatic ring system containing a 5- or 6-membered ring, said B(1) or B(2) being substituted with 2 or 3 groups of the formula OR$_1$, wherein R$_1$ represent H or a hydroxy-protecting or hydroxy-coupling group capable of protecting or coupling a hydroxy group during synthesis of a polynucleotide, or 2 groups when OR$_1$ represents a nucleotide or a polynucleotide connected to the remainder of said formula, and wherein one to three carbon atoms of the hydrocarbon group may be replaced by a nitrogen, or sulfur atom; or B represents a group of a third sub-formula

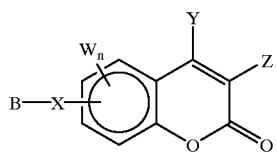

wherein
R$_x$, R$_y$, and R$_z$ independently represent OR$_1$;
m, n, p, q, and r independently represent 0 or 1; and
one hydrogen of said sub-formula is replaced by a covalent bond to said
X group;
X represents (1) a bond, (2) a linear, branched, or cyclic hydrocarbon group containing 1 to 10 carbon atoms or (3) said X(2) group in which one to three carbon atoms of the hydrocarbon group are replaced by an oxygen, sulfur, or nitrogen atom, and wherein the shortest linking chain of atoms in X between atoms in other parts of said formula attached to X is 1 to 10 atoms, wherein X is optionally substituted with 2–3 substituents selected from the group consisting of hydroxy, halogen, amino, amido, azido, carboxy, carbonyl, perfluoromethyl, and cyano functional groups; and wherein X is attached to the benzo ring of said formula directly or through W;
n is 1, 2, or 3;
each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms; or said hydrocarbyl group substituted with 2–3 of said functional groups or in which one carbon atoms replaced by an oxygen, sulfur, or nitrogen atom and wherein two Ws together can represent a ring fused to the benzo ring of said formula;
with the provisos that (1) when X or W is a substituted hydrocarbon, the total number of substituents in X or W is less than the total number of carbon atoms in said X or W and no more than one substituent or heteroatom is attached to a given carbon, unless said substituents are halogen atoms on said given carbon, and (2) the total carbon atoms in all W substituents is 15 or fewer; and
Y and Z independently represent H or lower alkyl.
28. The compound of claim 27, wherein X, in either orientation, is

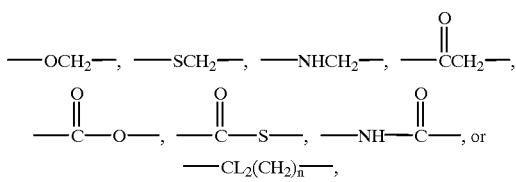

in which L=H, F, Cl, I, or Br and n=0, 1, or 2.

29. The compound of claim 27, wherein X is a cyclic structure with a 5- or 6-membered ring or a 5- or 6-membered heteroring containing one O, S, or N atom.

30. The compound of claim 27, wherein W is a pyrone or furan fing fused to the phenyl ring of said formula.

31. The compound of claim 27, wherein all of said formula to the right of X represents psoralen, cis-benzodipyrone, or trans-benzodipyrone.

32. The compound of claim 27, wherein X is covalently connected to the 4 position of a furan ring of a psoralen moiety.

33. The compound of claim 27, wherein B represents:

a group of a first sub-formula

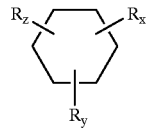

a group of a second sub-formula

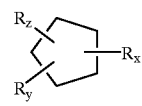

and all other substituents and definitions of said formula of said compound are otherwise as previously defined.

34. The compound of claim 27, wherein B is saturated.

35. The compound of claim 27, wherein B has said third sub-formula.

36. The compound of claim 35, wherein m+n+p+q+r=0, 1, or 2.

37. The compound of claim 36, wherein B represents an acyclic, saturated, tri-hydroxyhydrocarbon.

38. The compound of claim 36, wherein B represents tri-O-substituted glycerin.

39. The compound of claim 27, wherein at least one $R_1$ represents a trityl, pixyl, dimethoxytrityl, monomethoxytrityl, phosphite, phosphoramidite, phosphate, H-phosphonate, phosphorothioate, methylphosphonate, phosphorodithioate or phosphotriester group.

40. The compound of claim 27, wherein B contains a heterocyclic ring selected from the group consisting of pyrrole, pyrazole, imidazole, piperidine, pyridine, pyrazine, pyrimidine, pyridazine, thiophene, acridine, indole, quinoline, isoquinoline and quinazoline.

41. A compound of claim 27, wherein said compound is a polynucleotide of the formula $(N_{m1}Q_{m4}N_{m2})_{m3}$ in which each N represents a nucleotide of a desired polynucleotide sequence, Q represents the nucleotide-replacing molecule in the formula of claim 1, and m1, m2, and m3 are integers, and m3 is from 1 to 10.

* * * * *